United States Patent [19]

McCoy et al.

[11] 4,102,744
[45] Jul. 25, 1978

[54] TWO PHASE FERMENTATION

[75] Inventors: Carleton J. McCoy, Union, N.J.; Robert D. Schwartz, Charleston, W. Va.

[73] Assignee: Exxon Research & Engineering Co., Linden, N.J.

[21] Appl. No.: 752,277

[22] Filed: Dec. 20, 1976

[51] Int. Cl.² .............................. C12B 1/00; C12B 1/20
[52] U.S. Cl. .................................... 195/28 R; 195/117
[58] Field of Search .............................. 195/28 R, 117

[56] References Cited

U.S. PATENT DOCUMENTS

| 3,630,843 | 12/1971 | Furuya et al. | 195/28 R |
| 3,926,726 | 12/1975 | Antonini | 195/30 |

FOREIGN PATENT DOCUMENTS

| 45-29196 | 8/1971 | Japan | 195/28 N |

OTHER PUBLICATIONS

Schwartz, Applied Microbiology, Apr. 1973, pp. 574–577.
May et al., Biochmica et Biophysica Acta 1975, vol. 403, pp. 245-255.

Primary Examiner—Lionel M. Shapiro
Attorney, Agent, or Firm—Ronald D. Hantman; Albert P. Halluin

[57] ABSTRACT

A two phase fermentation system containing an aqueous nutrient medium plus a high concentration of organic solvent enables a suspension of microorganisms to convert a hydrocarbon substrate to product with a higher conversion frequency than a conventional aqueous phase fermentation. Further, the product is simultaneously extracted and concentrated in the organic phase, aiding in product recovery.

28 Claims, 1 Drawing Figure

TWO PHASE FERMENTATION

BACKGROUND OF THE INVENTION

This invention relates to a process for adding cyclohexane to a fermentation broth in order to maintain an inhibiting substance in the fermentation broth at a level which will permit continued fermentation.

Many fermentation processes involve chemical reactions carried out by microorganisms which convert certain organic compounds to other compounds. The process may or may not occur in the presence of air. The microorganisms produce enzymes which serve as catalysts for the chemical reactions. A common characteristic of these fermentations is that the end product of the process is in dilute aqueous solution. Recovery of the product from this solution often contributes signficantly to final product cost. Another characteristic shared by many fermentations is that continued biosynthesis of the product is inhibited in the presence of relatively low concentrations of the product itself, or the microorganism responsible for the fermentation may be impaired by the fermentation product. As a result, it is unusual to find fermentations in which the product occurs in high concentration.

Methods for removing or isolating inhibitory fermentation products include centrifugation, dialysis, ion exchange resins, and ultrafiltration. Centrifugation is generally quite expensive and may damage the microorganism. Ion exchange resins have been incorporated in fermentation broths to trap end products, but the resins are relatively expensive to use and they may also remove essential nutrients needed for growth. Dialyzing fermentation broths can remove fermentation products without damaging the microorganisms, but dialysis is also very expensive. Ultrafiltration is also expensive and fouling or plugging of the membrane may preclude its use in fermentation.

Therefore, an alternate process to prevent the product concentration from rising to a point where product biosynthesis is inhibited is desirable. By achieving these goals, a batch fermentation process could be made continuous, higher productivities could be reached, and product recovery costs could be reduced. The requirements for removing or isolating inhibitory products for use in this type of process are the following:

1. Rapid removal or isolation of product.
2. Non-toxic to the microorganism.
3. Must not remove the microorganism.
4. Must function at a neutral (or other suitable) pH.
5. Must not remove nutrients required for growth and/or product production by the microorganisms.

Recently, several reports have appeared in the literature on the use of non-aqueous solvents in conjunction with enzymic transformations. If developed, such systems could find use in enzymatic conversion processes, particularly those where the substrate and/or product(s) are water insoluble. Those systems dealing with whole microbial cells have used very high concentrations of pre-grown cells and high solvent concentrations, see Buckland, B. C., P. Dunnill, and M. D. Lilly, The enzymatic transformation of water-insoluble reactants in nonaqueous solvents: Conversion of cholesterol to cholest-4-ene-3-one by a *Nocardia* species, Biotechnol. Bioeng. 17:815–826, (1975); or low concentrations of solvent were used to pretreat the cells, see Martin, C. K. A. and D. Perlman, Stimulation by organic solvents and detergents of conversion of L-sorbose to L-sorbosone by Gluconobacter melanogenus IFO 3293, Biotechnol. Bioeng. 17:1473–1483, (1975). In the former case an 8-fold increase in conversion of substrate to product was observed, relative to aqueous controls, although the cells had been pre-grown and stored until used. In the latter, conversions were increased 2–3 fold although the effective solvents were toxic to the cells.

The present invention provides a new method for removal or isolation of an inhibitory product from a fermentation broth which meets the requirements listed above, in particular, simultaneous growth of the microorganism and isolation of the inhibitory products without toxicity to the microorganism.

SUMMARY OF THE INVENTION

Figure 1:
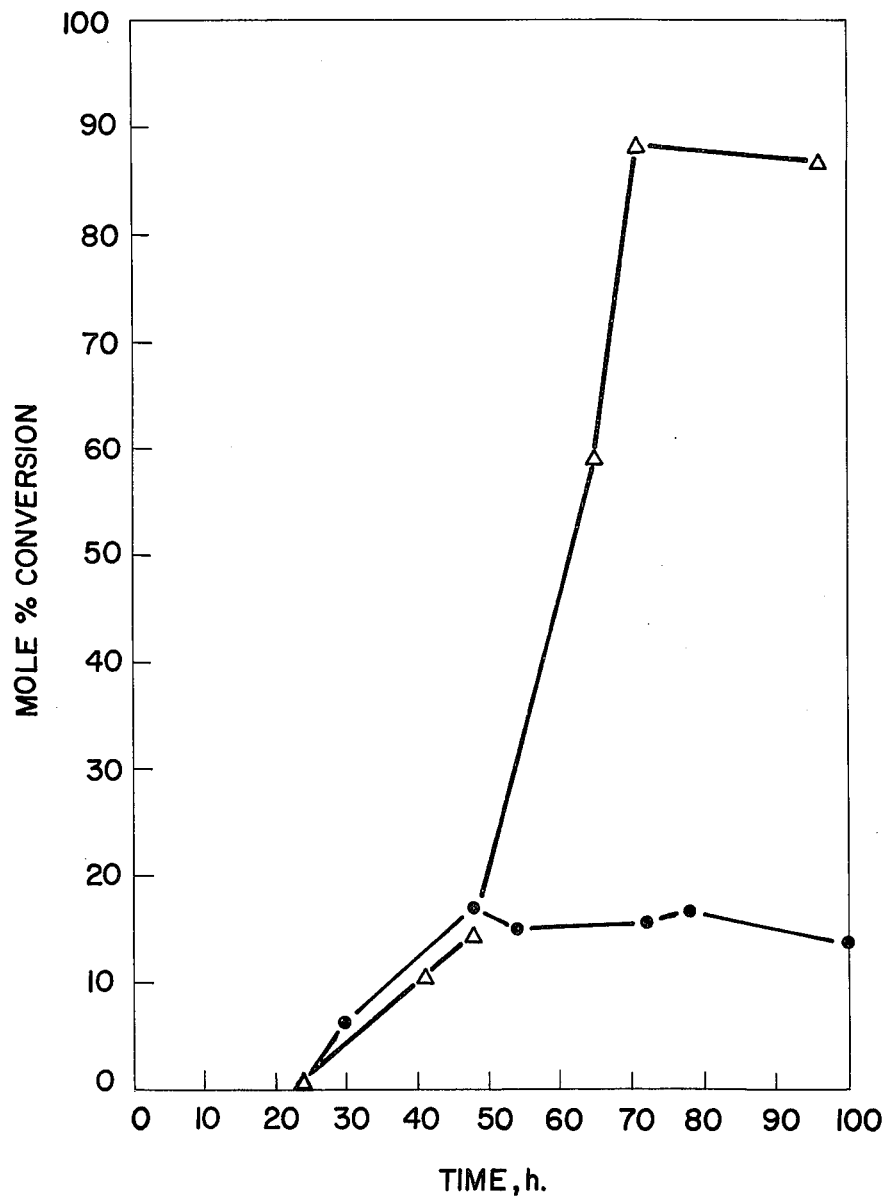
FIG. 1 is a graph showing the mole % conversion v. time of 1,7-octadiene to 7,8-epoxy-1-octene in aqueous medium in the absence (the O curve) and the presence (the Δ curve) of 20% cyclohexane.

The present invention, broadly, is a process for the transformation of a substrate by a microorganism within a fermentation broth including an aqueous nutrient medium, resulting in products, in which the substrate and/or one or more of the fermentation products inhibit continued fermentation, which comprises adding cyclohexane to the fermentation broth in an amount sufficient than at least one of the fermentation inhibitors is maintained at a level which will permit continued fermentation.

Another embodiment of the present invention pertains to a process for conducting an enzymatic transformation of a hydrocarbon substrate comprising conducting the enzymatic transformation in a two-phase fermentation system containing an aqueous nutrient medium and an organic solvent comprising cyclohexane and obtaining a hydrocarbon conversion product from said enzymatic transformation.

In still another embodiment of the present invention there is provided a process for the transformation of a substrate by a microorganism of the species *Pseudomonas oleovorans* which comprises conducting said transformation in an aqueous fermentation broth containing an aqueous nutrient medium and cyclohexane, said cyclohexane being maintained at a level wherein fermentation and transformation continues to take place.

In a preferred embodiment, the microorganism responsible for the enzymatic conversion of the substrate is *Pseudomonas oleovorans*, in particular, *Pseudomonas oleovorans* ATCC 29347 and the substrate is selected from the group consisting of 1-alkenes with formula $C_nH_{2n}$, where $5 \leq n < 12$, dienes with formula $CH_2=CH-(CH_2)_n-CH=CH_2$, $1 \leq n \leq 8$ and normal alkanes with formula $C_nH_{2n+2}$, $5 \leq n \leq 12$.

DESCRIPTION OF THE PREFERRED EMBODIMENT

The fermentation broth includes a substrate, a microorganism and an aqueous nutrient medium. After the microorganism begins the enzymic conversion of the substrate, the products also are included in the fermentation broth. The fermentation products produced from the enzymic conversion of the initial substrate may serve as a substrate for further enzymic conversion by the microorganism, e.g., see example 2 below. If the substrate or fermentation products exceed certain levels depending on the particular material, the microorganism or the enzymic activity may be inhibited. All those materials which inhibit continued fermentation must have low solubility in the aqueous phase. Then if a solvent for these inhibitory materials which is also insoluble in the aqueous phase such as cyclohexane is added to the broth that does not itself inhibit or harm the microorganism, the solvent will maintain the inhibitory materials at a level that will permit continued fermentation. While it is known that solvents are generally harmful to microorganisms, surprisingly, the cyclohexane did not interfere with the conversion process.

If the substrate is an organic material such as a hydrocarbon selected from one of the following: straight-chain alkene, $C_nH_{2n}$, $5 \leq n \leq 12$; straight-chain diene, $C_2H_{2n-2}$, $5 \leq n \leq 12$ straight chain alkane, $C_nH_{2n+2}$, $5 \leq n \leq 12$, then any microorganism that will oxidize this substrate and not be harmed by the solvent specified above, will continue to synthesize the products to a greater extent than if the solvent were absent. For example, such microorganisms include *Pseudomonas oleovorans*, and, in particular, *Pseudomonas oleovorans* ATCC 29347.

Preferred substrates include 1-alkenes with formula $C_nH_{2n}$, where $5 \leq n \leq 12$, dienes with formula $CH_2=CH-(CH_2)_n-CH=CH_2$ where $1 \leq n \leq 8$ and normal alkanes with the formula $C_nH_{2n+2}$ where $5 \leq n \leq 12$.

Some of the substrates listed above will not support cell growth and additional material must be included in the fermentation broth. Therefore, the broth may include a transformation substrate which provides the desired fermentation product and a growth substrate to provide for growth of the microorganism. The growth substrate must satisfy the same requirements as the transformation substrate, namely, all inhibitory growth substrates and their primary products (i.e., alcohols, aldehydes, acids) must have low solubility in the aqueous phase. The growth substrate may be selected from the substrates listed above if the substrate supports growth and satisfies the above requirements, e.g., n-octane. Other substrates, not listed above, that satisfy the above requirements, may also be used as a growth substrate. One skilled in the art will know which substrates serve as growth substrates. If the transformation substrate will support growth, then the transformation substrate and the growth substrate are the same material.

The amount of the solvent added to the fermentation broth may vary over a wide range from about 10 to 60% by volume. A preferred range is 15 to 25% by volume.

The amount of either substrate may also vary over a range from very small amounts (say, 0.1% by volume) to concentrations approximately equal to 15% by volume. A preferred range is 1 to 8% by volume. However, the ratio of growth substrate to the transformed substrate, if they are different, must be such that growth of the microorganism is not inhibited as a result of competitive inhibition between the growth substrate and the transformed substrate. Therefore, the transformed substrate should not exceed about 5 times the amount of the growth substrate. A preferred amount for each of the substrates is about ½ to 1½% by volume.

The process should be practiced at a temperature maintained between 15° and 40° C. A preferred temperature range is between 28° and 34° C.

The process should be practiced with the pH of the aqueous broth maintained between 6 and 8. A preferred range is 6.8 to 7.4. The period of time required for maximum conversion of the transformed substrate depends on the particular reaction and the initial concentration of the microorganism. In general, one to five days should be sufficient although it is preferable initially to include a high enough inoculum of microorganism so that the period of time for maximum conversion is between one and three days.

The microorganism *P. oleovorans* TF4-1L (ATCC 29347) has been studied extensively in the prior art. The organism, medium, growth conditions, and assays have been described in the literature, see, e.g., Schwartz, R. D., Octene epoxidation by a cold-stable alkane-oxidizing isolate of *Pseudomonas oleovorans*, Appl. Microbiol. 25:574–577 (1973); May, S. W., R. D. Schwartz, B. J. Abbott, and O. R. Zaborsky, Structural effects on the reactivity of substrates and inhibitors in the epoxidation system of *Pseudomonas oleovorans*, Biochim, Biophys, Acta 403: 245–255 (195); Schwartz, R. D. and C. J. McCoy, Enzymatic epoxidation synthesis of 7,8-epoxy-1-octene, 1,2-7,8-diepoxyoctane, and 1,2-epoxyoctane by *Pseudomonas oleovorans*, Appl. Environ. Microbiol, 31:78–82 (1976), which are incorporated by reference in this application. However, for convenience, some of the results contained in those papers are repeated here. Table 1 lists the composition of the medium.

TABLE 1

| COMPOSITION OF MINIMAL SALTS MEDIUM | |
|---|---|
| Compound | Amount |
| $(NH_4)_2HPO_4$ | 10.0 g |
| $K_2HPO_4$ | 5.0 g |
| $Na_2SO_4$ | 0.5 g |
| $CaCl_2$(50 g/L) | 1.0 ml |
| Salts "B" | 10.0 ml |
| $MgSO_4 \cdot 7H_2O$ | 40.0 g |
| $FeSO_4 \cdot 7H_2O$ | 2.0 g |
| $MnSO_4 \cdot H_2O$ | 1.6 g |
| NaCl | 2.0 g |
| Distilled water | 1 liter |
| Microelements | 1.0 ml |
| $H_3BO_3$ | 0.50 g |
| $CuSO_4 \cdot 5H_2O$ | 0.20 g |
| $ZnSO_4 \cdot 7H_2O$ | 8.00 g |
| $CuCl_2 \cdot 6H_2O$ | 0.20 g |
| Distilled Water | 1 liter |
| Distilled water | 1 liter |

As noted in the prior art cited above and in the preceding discussion, some of the substrates will not support cell growth and, therefore, additional growth material must be included in the broth. For example, if 1,7-octadiene is to be epoxidated by the enzyme system, octane is included in the fermentation broth as a growth substrate.

The minimal salts medium (Table 1) plus substrate is inoculated with the microorganism to form a fermentation broth. But, as the following examples show, conversion of the substrate to fermentation products is limited by the fermentation products. However, if a solvent, cyclohexane, is added to the broth, conversion of the substrate to products is increased severalfold.

EXAMPLE 1

Enzymic epoxidation of 1,7-octadiene using the enzyme system of Pseudomonas oleovorans The mechanism of enzymic epoxidation using an enzyme system in *Pseudomonas oleovorans* ATCC 29347 was studied in this example. In order to study the nature of the products formed from the epoxidation of 1,7-octadiene, it was necessary to synthesize and recover gram quantities of the products: 7,8-epoxy-1-octene;

1,2-7,8-diepoxyoctane. Initially, conventional fermentation was used, i.e., an aqueous minimal salts medium containing both octane (1% vol/vol) and 1,7-octadiene (1% vol/vol) was inoculated with *P. oleovorans* and incubated for about 30 hours at 30° C. During this time growth occurred at the expense of octane, and the octadiene was epoxidized. In this system the product yields were at best 1-1.2 g of 7,8-epoxy-1-octene/L and 0.3-0.4 g of 1,2-7,8-diepoxyoctane/L. One of the limiting factors was the inhibition observed when the concentration of 7,8-epoxy-1-octene reached about 0.8 g/L, see the Schwartz et al paper referred to above. The results are included in Table 2 and FIG. 1.

If the concentrations of the organic substrates and products could be maintained at a low (subinhibitory) level in the aqueous phase, substantial yield improvements might be obtained. The aqueous fermentation medium was modified so as to contain an appropriate amount of a nonaqueous solvent, cyclohexane, and the fermentaion was conducted as before. The results of this mixed phase fermentation are presented in the next example.

EXAMPLE 2

Enzymic epoxidation according to the present invention

The materials were the same as in Example 1, except for the addition of cyclohexane.

Experiments with growing cells were conducted in 300 ml baffled shake flasks containing 100 ml of medium supplemented with 1,7-octadiene and n-octane (1%, vol/vol each), at 30° C. The medium was modified so as to contain the indicated amount of cyclohexane (vol/vol).

Unless otherwise indicated, the entire contents of the shake flask were centrifuged to separate the phases and the volume of each phase was measured and assayed for epoxides.

FIG. 1 and Table 3 shows the conversion of 1,7-octadiene to 7,8-epoxy-1-octene and 1,2-7,8-diepoxyoctane by cells growing on n-octane, in the presence (the Δ curve) and absence (the o curve) of 20% (vol/vol) cyclohexane. At time zero a series of identical shake flasks were inoculated. One flask was removed and the contents were assayed at each of the times indicated. In the absence of cyclohexane the epoxides reached a maximum concentration of 1.6 g/L, or 18.5 mol % conversion of 1,7-octadiene. In the presence of cyclohexane 7.49 g epoxides/L accumulated (88.9 mol % conversion). There was visible cell growth shortly after the appearance of epoxide in both the presence and absence of cyclohexane. By the end of the experiment, all flasks contained heavy cell suspensions.

Table 3 shows the distribution of the epoxides among the cyclohexane phase (20 ml), aqueous phase (80 ml), and cell pellet. Ninety to 95% of the epoxides were found to be associated with the cyclohexane phase. However, whereas 95% of the monoepoxide (7,8-epoxy-1-octene) is found in the cyclohexane throughout the fermentation, the diepoxide (1,2-7,8-diepoxyoctane) became more evenly distributed between the aqueous and non-aqueous phases. Note also that the monoepoxide represents 95% or more of the total epoxide products through 71 h, and was 87% at 96 h. After 71 h of fermentation, 85% of the cyclohexane was recovered; at 96 h, 75% was recovered. Hence, not only was the conversion of 1,7-octadiene to epoxides enhanced about five-fold in the presence of cyclohexane, but the epoxides were simultaneously concentrated in the non-aqueous solvent.

In summary, *P. oleovorans* ATCC 29347, growing at the expense of n-octane and in the presence of 1,7-octadiene, oxidized the octadiene to epoxide products at an efficiency approaching 90 mol % conversion. This was accomplished by incorporating a water-insoluble organic solvent, cyclohexane, into the conventional aqueous fermentation medium. Further, the presence of the cyclohexane resulted in the simultaneous separation and concentration of the products in the organic phase. The modified fermentation results in a five-fold increase in efficiency of conversion of 1,7-octadiene to 7,8-epoxy-1-octene and 1,2-7,8-diepoxyoctane relative to the conversion in conventional aqueous medium.

It was stated above that in aqueous medium the monoepoxide was toxic to the cells at a concentration of about 0.8 g/L. In the presence of cyclohexane, the monoepoxide concentration in the aqueous phase (in which the cells are suspended) reached only about half this value; the rest was found in the cyclohexane. This is expected because the monoepoxide is much more soluble in the cyclohexane than in the water. Hence, the cells per se were never exposed to inhibitory concentrations of the monoepoxide and the reaction proceeded virtually to completion. The diepoxide, however, is more water soluble and was eventually found equally distributed between the two phases.

TABLE 2

Epoxidation of 1,7-octadiene in Conventional Aqueous Fermentation and Combined Aqueous Phase and Solvent Phase Fermentation. Initial Octadiene Concentration 7.32 g/L

| | Product Synthesis in | | | |
|---|---|---|---|---|
| | Conventional Aqueous | | Mixed Phase 80% Aqueous 20% Cyclohexane | |
| Product Recovered From | 7,8-epoxy-1-octene | 1,2-7,8-diepoxyoctane | 7,8-epoxy-1-octene | 1,2-7,8-diepoxyoctane |
| Aqueous Phase | 1.2 g/L | 0.4 g/L | 0.19 g/L | 0.25 g/L |
| Cyclohexane Phase | — | — | 6.7 | 0.27 |
| Cell Pellet | — | — | 0.08 | 0 |
| Molar Conversion to Products, % | 14.3 | 4.2 | 83.3 | 5.6 |

TABLE 3

Distribution of Epoxides Among Solvent Phase, Aqueous Phase and Cell Pellet in Combined Aqueous Phase and Solvent Phase Fermentation. The Results are Shown as the Total Amount of Product Found in Each Phase. Initial Substrate Concentration was $6.65 \times 10^{-3}$ moles, 1,7-octadiene.

| Time | Volume Recovered | | 7,8-epoxy-1-octene, μMoles | | | 1,2-7,8-diepoxyoctane, μMoles | | |
|---|---|---|---|---|---|---|---|---|
| | Solvent | Aqueous | Solvent | Aqueous | Cell Pellet | Solvent | Aqueous | Cell Pellet |
| 24 h | 20 ml | 80 ml | 5.3 | 0 | 0 | 0 | 0 | 0 |
| 41 | 20 | 80 | 661 | 35 | 0.5 | 0 | 0 | 0 |
| 48 | 18 | 80 | 924 | 28 | 10.4 | 19 | 0 | 0 |
| 65 | 17 | 80 | 3437 | 301 | 14.5 | 174 | 0 | 10.4 |
| 71 | 17 | 80 | 5283 | 300 | 14.7 | 145 | 131 | 9.1 |
| 96 | 15 | 77 | 4762 | 200 | 47.3 | 376 | 352 | 30.4 |

EXAMPLE 3

Effect of increasing the solvent concentration on the enzymatic system of Example 2

Although it would appear to be preferable to use the lowest concentration of non-aqueous solvent giving the maximum conversion, so as to maximize the product extraction and concentration effect, concentrations of cyclohexane up to 60% were tested. As shown in Table 4, the major effect of increasing the cyclohexane concentration was to increase the lag time before epoxide formation (and cell growth) is observed. Eventually, comparable conversions were obtained at all cyclohexane concentrations tested.

Even though cell growth was delayed in the presence of cyclohexane concentrations as high as 60% vol/vol, the fermentation proceeded to completion. Again, the cells apparently were not exposed to toxic levels of cyclohexane or 7,8-epoxy-1-octene. The smallest amount of non-aqueous solvent giving maximum conversion in the shortest period of time is preferable so as to maximize the product concentration effect. In the present case this was 20% vol/vol. Although lower concentrations will work, experiments using lower concentrations led to significant solvent losses and difficulties in phase separation when shake flasks were used. These problems can doubtless be overcome by modifying the fermentation system, i.e., continuous fermentation with vapor phase condensation and recycle.

TABLE 4

Effect of Increasing Solvent Concentration on Epoxidation. Phases Not Separated Prior to Assay.
7,8-epoxy-1-octene Plus 1,2-7,8-diepoxyoctane, μmoles/ml.

| | Cyclohexane Concentration, % | | | | | |
|---|---|---|---|---|---|---|
| Time, h | 0 | 20 | 30 | 40 | 50 | 60 |
| 24 | 0 | 0 | 0 | 0 | 0 | 0 |
| 30 | 4.2 | 0.2 | 0 | 0 | 0 | 0 |
| 48 | 11.1 | 21.8 | 6.4 | 8.8 | 0 | 0 |
| 54 | 10.1 | 20.9 | 7.1 | — | Trace | 0 |
| 72 | 10.5 | 27.2 | 13.9 | 30.6 | 5.2 | 0 |
| 78 | 11.1 | 48.2 | 36.2 | 24.3 | 29.0 | 0 |
| 100 | 9.2 | 35.8 | 24.5 | 34.3 | 43.3 | 0 |
| 173 | 5.3 | 31.2 | 34.0 | 54.9 | 54.7 | 25.5 |

What is claimed is:

1. A process for the oxidative enzymatic transformation of a $C_5$ to $C_{12}$ linear hydrocarbon substrate by a microorganism of the species *Pseudomonas oleovorans* which comprises conducting said enzymatic transformation in an aqueous fermentation broth containing an aqueous nutrient medium and cyclohexane, said cyclohexane being maintained at a level wherein fermentation and enzymatic transformation continues to take place.

2. A process for conducting an oxidative enzymatic transformation of a linear hydrocarbon substrate comprising conducting the enzymatic transformation in a two-phase fermentation system containing an aqueous nutrient medium and an organic solvent comprising cyclohexane and obtaining an oxidative hydrocarbon conversion of said linear hydrocarbon substrate product from said enzymatic transformation.

3. The process of claim 2 wherein the substrate is selected from the group consisting of straight chained alkanes with the formula $C_nH_{2n+2}$, $5 \leq n \leq 12$; straight chain alkenes with formula $C_nH_{2n}$, $5 \leq n \leq 12$; and straight chain dienes with formula $C_nH_{2n-2}$, $5 \leq n \leq 12$.

4. The process of claim 2 wherein said substrate is a straight chain alkane with the formula $C_nH_{2n+2}$ where $n$ may take on any value between and including 5 and 12.

5. The process of claim 3 wherein said substrate is a straight chain alkene with the formula $C_nH_{2n}$ where $n$ may take on any values between the including 5 and 12.

6. The process of claim 3 wherein said substrate is a straight chain diene of the formula $C_2H_{2n-2}$ wherein $n$ may take on any value between and including 5 and 12.

7. The process of claim 6 wherein said substrate is a diene of the formula $CH_2=CH-(CH_2)_n-CH=CH_2$ where $n$ may take on any value between and including 1 and 8.

8. The process of claim 3 wherein said substrate includes a transformation substrate and a growth substrate.

9. The process of claim 3 wherein the enzyme is derived from a microorganism of the species *Pseudomonas oleovorans*.

10. A process for conducting an enzymatic transformation of a hydrocarbon substrate by a microorganism of the species *Pseudomonas oleovorans* within a fermentation broth including an aqueous nutrient medium, resulting in products, in which said substrate and/or one or more of said fermentation products inhibit continued fermentation, which comprises adding cyclohexane to said fermentation broth in an amount sufficient such that at least one of the fermentation inhibitors is maintained at a level which will permit continued fermentation.

11. The process of claim 1 wherein said microorganism is *Pseudomonas oleavorans* ATCC 29347.

12. The process of claim 1 wherein the substrate is selected from the group consisting of straight chain alkanes with formula $C_nH_{2n+2}$, $5 \leq n \leq 12$; straight chain alkenes with formula $C_nH_{2n}$, $5 \leq n \leq 12$; and straight chain dienes with formula $C_nH_{2n-2}$, $5 \leq n \leq 12$.

13. The process of claim 12 wherein said substrate is a straight chain alkane with the formula $C_nH_{2n+2}$ where $n$ may take on any value between and including 5 and 12.

14. The process of claim 12 wherein said substrate is a straight chain alkene with the formula $C_nH_{2n}$ where $n$ may take on any values between and including 5 and 12.

15. The process of claim 12 wherein said substrate is a straight chain diene of the form $C_2H_{2n-2}$ where $n$ may take on any value between and including 5 and 12.

16. The process of claim 13 wherein said substrate is a normal alkane with the formula $C_nH_{2n+2}$ where $n$ may take on any value between and including 5 and 12.

17. The process of claim 14 wherein said substrate is a 1-alkene with the formula $C_nH_{2n}$ where $n$ may take on any values between and including 5 and 12.

18. The process of claim 15 wherein said substrate is a diene of the formula $CH_2\!=\!CH\!-\!(CH_2)_n\!-\!CH\!=\!CH_2$ where $n$ may take on any value between and including 1 and 8.

19. The process of claim 1 wherein said substrate includes a transformation substrate and a growth substrate.

20. The process of claim 16 wherein said growth substrate is n-octane.

21. The process of claim 1 wherein said cyclohexane is present in an amount between 10 and 60% by volume.

22. The process of claim 21 wherein said cyclohexane is present in an amount between 15 and 25% by volume.

23. The process of claim 1 wherein said process is conducted at a temperature between 15° and 40° C.

24. The process of claim 23 wherein said process is conducted at a temperature between 28° and 34° C.

25. The process of claim 1 wherein said process conducted at a pH between 6 and 8.

26. The process of claim 25 wherein said process conducted with a pH between 6.8 and 7.4.

27. The process of claim 1 wherein said substrate is present in an amount of 0.1 to 15% by volume.

28. The process of claim 19 wherein said transformation substrate and said growth substrate are each present in an amount of 0.5 to 1.5%.

* * * * *